United States Patent

Murakami et al.

[11] 4,413,520
[45] Nov. 8, 1983

[54] ULTRASONIC IMAGING APPARATUS

[75] Inventors: Keiichi Murakami, Kawasaki; Shinichi Amemiya; Junji Miyazaki, both of Yokohama; Tadahiko Yanashima, Fujisawa; Atsuo Iida, Yokohama; Takaki Shimura, Machida; Hirohide Miwa; Norio Midorikawa, both of Kawasaki, all of Japan

[73] Assignee: Fujitsu Limited, Kawasaki, Japan

[21] Appl. No.: 274,160

[22] Filed: Jun. 16, 1981

[30] Foreign Application Priority Data

Jun. 16, 1980 [JP] Japan ................... 56-21655

[51] Int. Cl.³ ............................. G01N 29/04
[52] U.S. Cl. ............................ 73/609; 73/628
[58] Field of Search .......... 73/609, 628, 617, 620; 128/660

[56] References Cited

U.S. PATENT DOCUMENTS 3,156,110 11/1964 Clynes ........................ 73/628
4,167,879 9/1979 Pedersen ....................... 73/620

FOREIGN PATENT DOCUMENTS

WO80/01537 7/1981 PCT Int'l Appl. .

Primary Examiner—Anthony V. Ciarlante
Attorney, Agent, or Firm—Staas & Halsey

[57] ABSTRACT

An ultrasonic imaging apparatus comprises transducers for transmitting ultrasonic waves and receiving acoustic. The apparatus also transmits ultrasonic waves of different frequencies simultaneously from a plurality of transducers.

The frequency characteristics of the transducers are determined in a manner so as to produce the function of frequency filters. An electric filter is additionally provided for compensation. Thus, crosstalk is eliminated even when the frequency difference between the transmitting ultrasonic waves is kept small.

13 Claims, 13 Drawing Figures

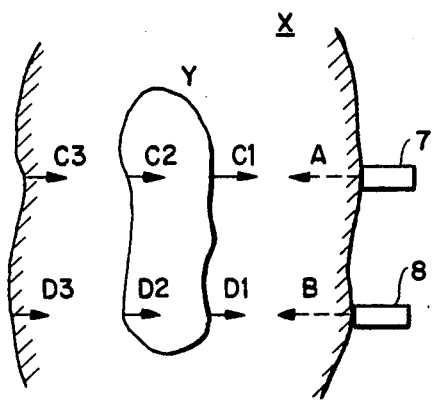
FIG. 1.
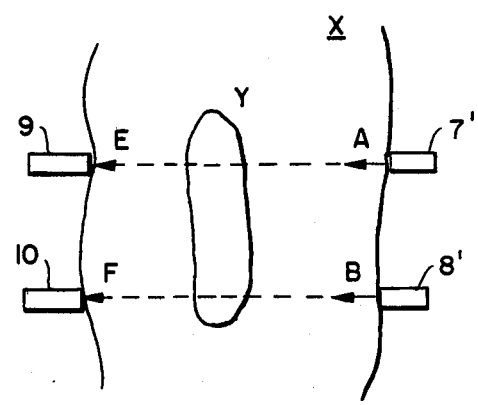
FIG. 2.
FIG. 3.
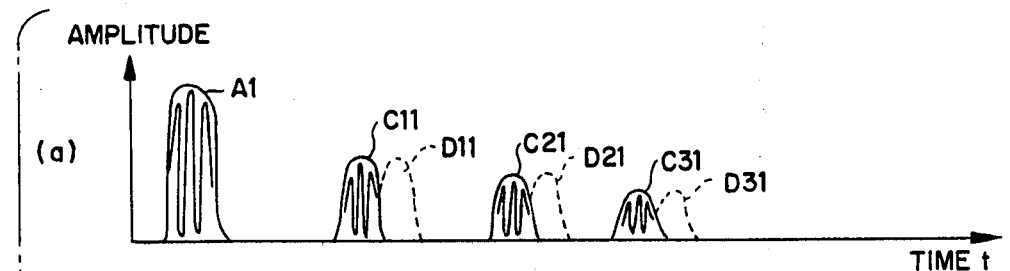
(a)
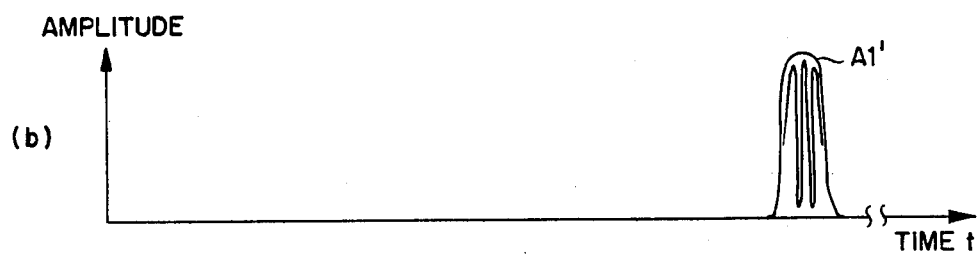
(b)
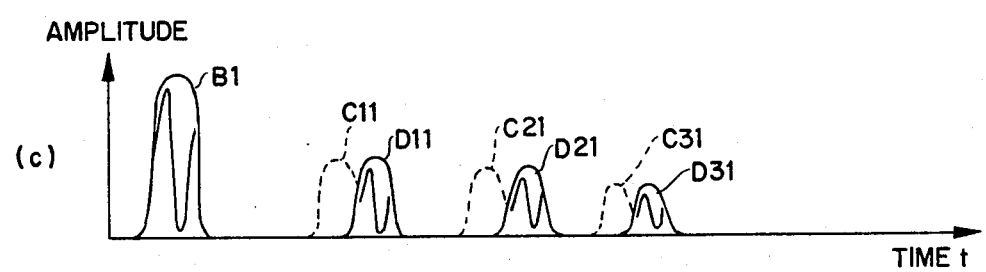
(c)
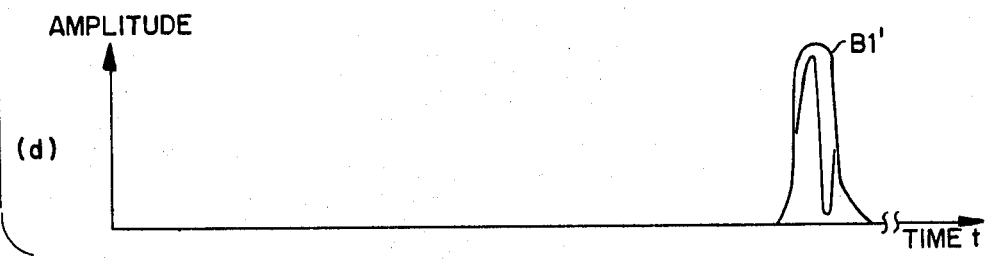
(d)

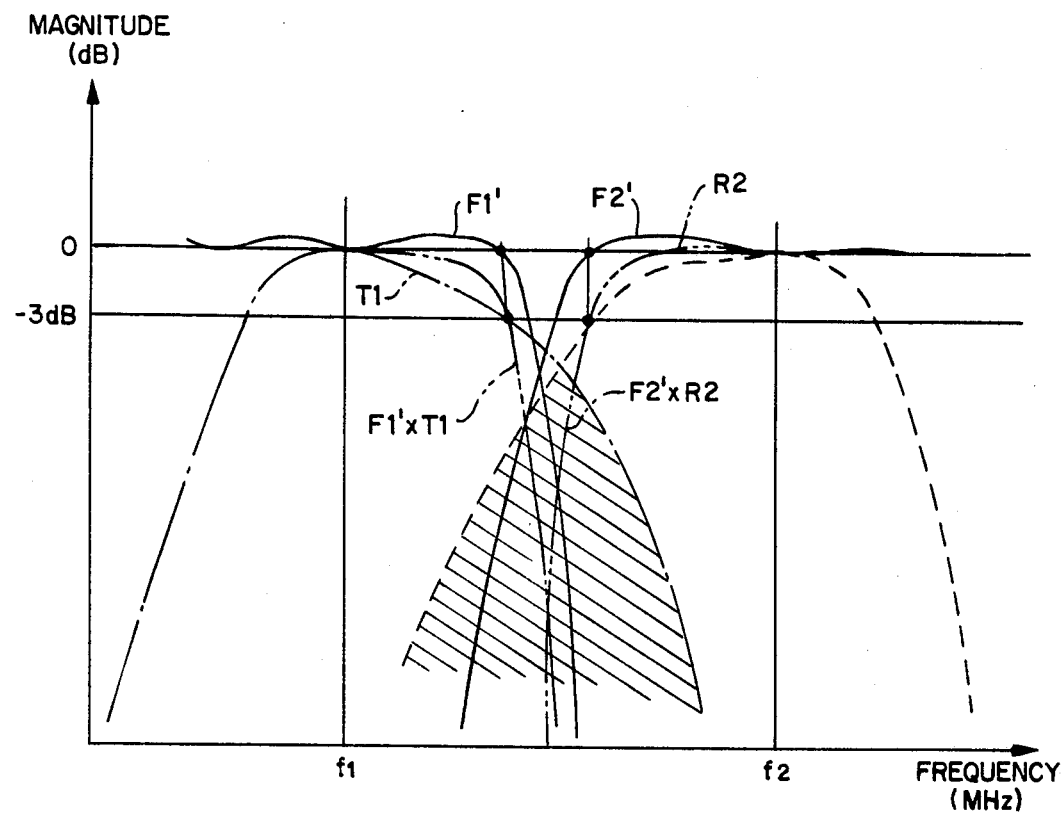
FIG. 10B.
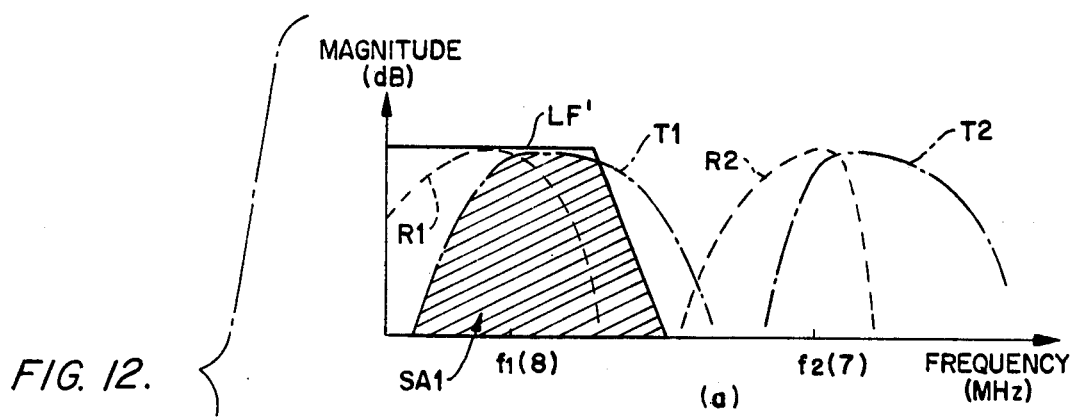
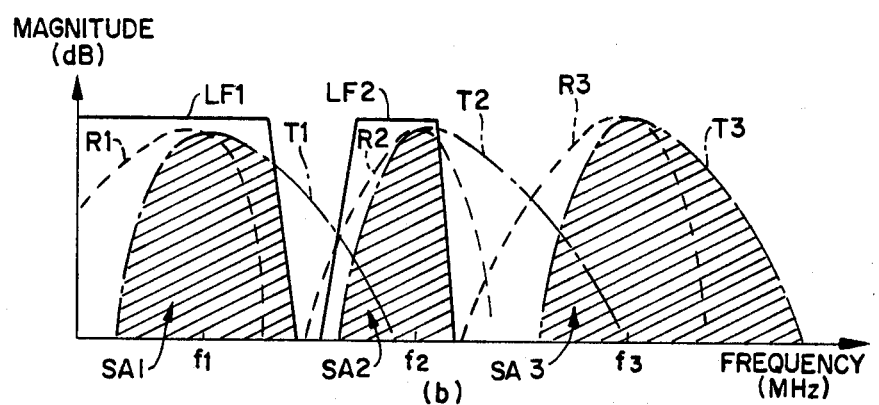
FIG. 12.

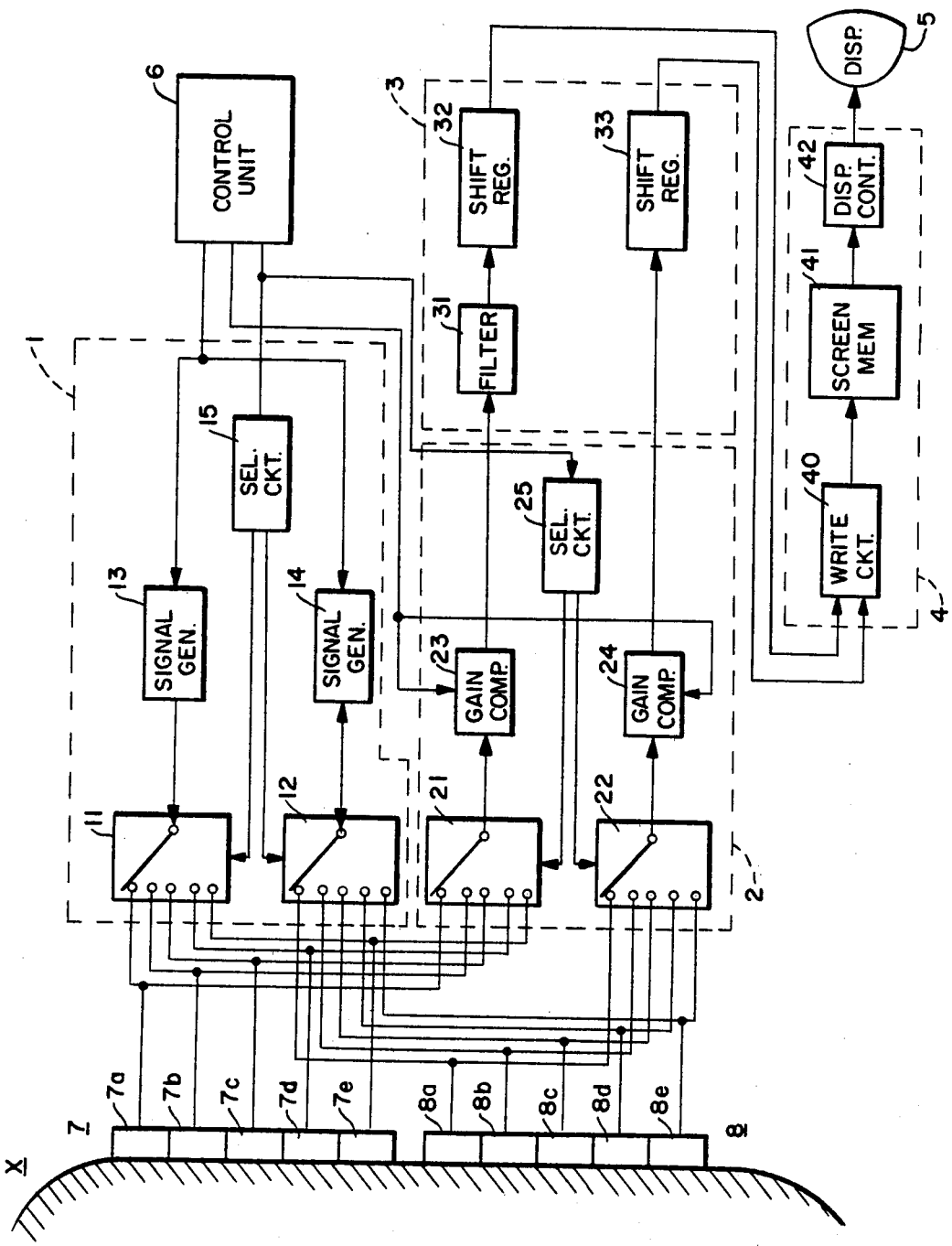

ULTRASONIC IMAGING APPARATUS

BACKGROUND OF THE INVENTION

1. Field of the Invention

This invention relates to an improvement in ultrasonic developing apparatus for imaging an internal image of an object by utilizing ultrasonic waves, and particularly to an improvement in an ultrasonic imaging apparatus which transmits ultrasonic waves to an object and receives the reflected waves or transmitted waves returning from the object.

2. Description of the Prior Art

Ultrasonic imaging technology is widely employed for obtaining an internal image of an object such as a human body.

In such technology, an ultrasonic wave is transmitted to an object, the reflected wave corresponding to the transmitted wave returning from the object is received, and then a tomographic image indicating tissues of an object is obtained on the basis of such a received wave. The ultrasonic imaging has advantages in that it is non-destructive and results in less danger as compared with the existing X-ray imaging.

In general, a widely known ultrasonic imaging apparatus utilizes the pulse reflection method which uses the reflected wave, and therefore the operation of such an ultrasonic imaging apparatus will be explained focusing on this pulse reflection method as an example. The ultrasonic wave pulse of about 1 MHz to 10 MHz is transmitted to an object from the piezoelectric element of a transducer, the echo pulse (reflected wave), which is reflected by a mismatching of impedance at the boundary of two tissues having different acoustic impedances within said object, is received, and the location information of said mismatching area can be obtained by displaying such a received wave. This is called the A mode operation.

A tomographic image can be obtained by the following steps. Namely, the ultrasonic wave pulse transmission location or angle is sequentially shifted according to the location of the tomographic area, and some pieces of location information at the mismatching areas are used for a display based on the data from the reflected waves of respective transmitted pulses. This is called the B mode operation.

In such an existing ultrasonic image apparatus, since the next ultrasonic wave pulse is transmitted after the sufficient time for the preceding ultrasonic wave pulse to be transmitted and then to return as the echo pulse, the period between transmission of ultrasonic wave pulses is resultingly limited to the period required for completing reception of the echo pulse.

Therefore, since the propagative velocity of ultrasonic waves in the tissues of a human body is about 1,500 m/sec, the period from transmission of pulse to reception of echo becomes 2L/1500 (sec) when the depth of boundary is L (meters), and the minimum pulse transmission period is 2L/1500 (sec).

Namely, the number of scanning lines obtained during a second is limited to 1500/2L (lines). For example, when L is 0.2 m, the number scanning lines is 3750 (lines) and therefore it is no longer possible to obtain sufficient scanning lines when a tomographic image is required within a very short period (for example, 0.1 sec).

Moreover, limitation on the number of scanning lines influences the display of a tomographic image on the CRT display unit.

Namely, since the frame rate of about 30 frame/sec is necessary for displaying the motion within an object without flickering, the number of scanning lines in one frame is limited to 25/L (lines). In other words, when L=0.2 m, the number of scanning lines becomes 125 lines/frame which is only ¼ of the scanning lines in television receivers. Therefore, such limitation on the number of scanning lines results in very rough display of a tomographic image, thereby reducing the image's effectiveness.

In addition, the existing ultrasonic wave imaging apparatus has the disadvantage that a sufficient number of scanning lines cannot be obtained; it is difficult to accurately image momentary conditions of dynamic tissues such as the heart, etc., of a human body and only a very rough display of a tomographic image can be obtained, due to the inherent limitation on the propagation velocity of ultrasonic waves. It has been a necessity for such apparatus to eliminate this disadvantage.

In order to solve such problems, two of the inventors of the present invention have proposed an improved ultrasonic imaging apparatus by the specification of the international patent application No. PCT/JP80/00015 titled "Ultrasonic Diagnostic System", which corresponds to U.S. application Ser. No. 209,403, filed Sept. 22, 1980.

According to this specification, the ultrasonic waves having different frequencies are simultaneously transmitted from a plurality of transducers, the reflected waves or transmitted waves reflecting from an object are received, and then those reflected waves or transmitted waves having specific, predetermined frequencies can be obtained from the total received signal using an electrical filter.

This technique presents simultaneously several times the internal information of the object as that of existing apparatus.

When a human body is selected as an object, attenuation in the object is generally high as the frequency becomes high.

Therefore, when employing the abovementioned technique, it is desirable that differences between plural frequencies are as small as possible, namely that the frequency $f_1$ of the one transmitting wave and the frequency $f_2$ of the other wave are very close.

However, when the frequencies $f_1$ and $f_2$ are very close, it is difficult to separate them sufficiently using only an electrical filter.

For this reason, even after the received signal has passed an electrical filter, so-called crosstalk occurs. In other words, the signal of the other frequency $f_2$ still remains in the signal of one frequency $f_1$.

SUMMARY OF THE INVENTION

It is an object of the present invention to provide an improved ultrasonic imaging apparatus which is easily capable of preventing the crosstalk between waves of different frequencies.

It is another object of the present invention to provide an improved ultrasonic imaging apparatus which is capable of preventing the crosstalk even when a very accurate and expensive electrical filter is not used.

It is a further object of the present invention to provide an improved ultrasonic imaging apparatus which offers accurately and simultaneously multiple internal information of the object.

It is a still further object of the present invention to provide an improved ultrasonic imaging apparatus which is suitable for searching internal tissues of a human body.

It is still another object of the present invention to provide an improved ultrasonic image apparatus which is capable of utilizing the transmission and reception frequency characteristics of transducers to perform a filtering function.

Accordingly, in the ultrasonic imaging apparatus of the present invention, at least two or more transducers for transmitting ultrasonic waves and receiving acoustic waves provide respectively different frequency characteristics, and the frequency characteristics shows are employed to perform the function of frequency filter.

The pertinent ultrasonic imaging apparatus comprises: a 1st transmission circuit which is connected to one transducer and which causes the one transducer to transmit ultrasonic waves of the 1st frequency; a 1st reception circuit which is connected to the one transducer; a 2nd transmission circuit which is connected to another transducer and causes the other transducer to transmit ultrasonic waves of the 2nd frequency which is different from that of the 1st frequency; and a 2nd reception circuit which is connected to the other transducer. Moreover, an electrical filter is provided in at least one of the 1st transmission circuit or the 2nd reception circuit.

For further complete elimination of crosstalk, an electric filter is also provided in the 2nd transmission circuit and the 1st reception circuit.

Thus, while the frequency characteristics of transducers are used in performing the filter function, the remaining elements not compensated thereby can then be compensated by the electrical filter.

BRIEF DESCRIPTION OF THE DRAWINGS

FIG. 1 and FIG. 2 are schematic diagrams which illustrate the basic principle of the present invention;

FIG. 3 is a time chart for the principle shown in FIG. 1;

FIGS. 10A and 10B are graphs of the characteristics of an electrical filter according to the present invention;

FIG. 11 is a block diagram of the preferred embodiment of the present invention;

FIG. 12 is a graph of the frequency characteristics of another embodiment of the present invention.

DESCRIPTION OF THE PREFERRED EMBODIMENTS

Figure 6:
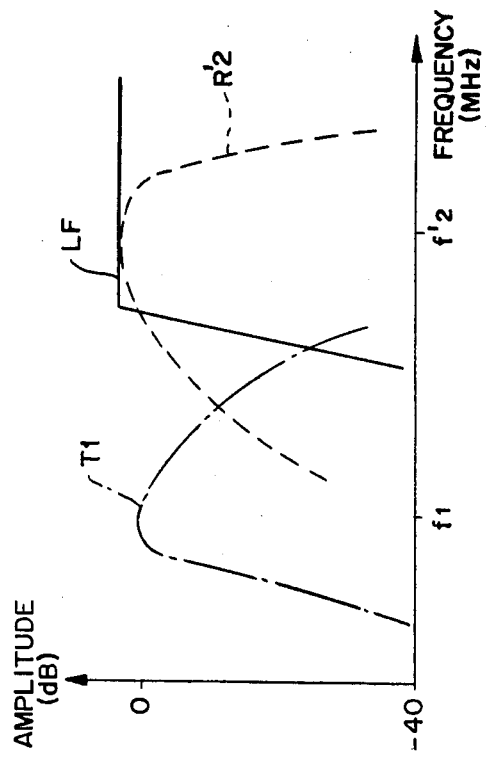
FIG. 6 and FIG. 7 are each graphs which show the frequency characteristics when an electrical filter is connected according to the present invention.

FIG. 1 and FIG. 2 illustrate the basic principle of the present invention. FIG. 1 shows an example of the reflection type. In this case, the transducers 7, 8 including the electro-acoustic conversion element transmit the ultrasonic waves A, B to the specimen. The two kinds of ultrasonic waves A, B respectively have different frequencies $f_2$, $f_1$.

The ultrasonic wave A is reflected at the area where the internal tissues changes within the specimen X, namely the reflected waves $C_1$, $C_2$ are returned from the boundary with the tissue Y, while the reflected wave $C_3$ from the boundary of the specimen X. In the same way, the reflected waves $D_1$, $D_2$ and $D_3$ are returned for the ultrasonic wave B.

These reflected waves are received by the 1st and 2nd transducers 7, 8 and converted to electical signals. However, the transducers 7, 8 receive not only the reflected waves for their own transmitting frequencies but also the reflected waves for the other frequency signal. In other words, each of the transducers 7, 8 receives both the reflected waves $C_1$ to $C_3$ and $D_1$ to $D_3$ and then converts them into electrical signals. At this time, in the case of the invention, as will be described later, the reflected waves $C_1$ to $C_3$ and those $D_1$ to $D_3$ are separated and extracted respectively by making use of the filtering characteristic of the transducers 7, 8. The extracted reflected waves in time series are used as the tomographic data of the location of transducers 7, 8.

In the case of reflection type, the transducers 7, 8 may also be used for transmission only instead being used in common for transmission and reception, and an electro-acoustic conversion element for the reception only is provided.

For the B mode operation, i.e. the so-called mechanical linear scanning method, the transducers 7, 8 are mechanically shifted and the electronic scanning method where many transducers 7, 8 are arranged in the form of an array and the scanning is performed electrically, are employed. In addition, the sector scanning method can also be introduced.

FIG. 2 shows an example of the attenuation type, where a couple of electro-acoustic conversion element pairs 7', 9 and 8', 10 are provided face to face, respectively.

The 1st and 2nd electro-acoustic conversion elements 7', 8' transmit the ultrasonic waves A, B to the specimen X. The ultrasonic waves A, B have different frequencies.

The attenuated wave E obtained after the ultrasonic wave A has passed through the specimen X including the tissue Y is received by 1st electro-acoustic conversion element 9 and is then converted into an electrical signal. In the same way, the transmitted wave F obtained after the ultrasonic wave has passed the specimen X including the tissue Y is received by the 2nd electro-acoustic conversion element 10 and is converted into an electrical signal. The electro-acoustic conversion elements 9, 10 receive both transmitted waves E, F as in the case of reflection type. Therefore, the transmitted waves E, F are separated and extracted by the band-pass characteristic of the elements 9, 10 themselves.

In the case of the attenuation type, it is possible to use only one among the electro-acoustic conversion elements 9, 10 for reception.

As in the case of reflection type, a tomographic image can be obtained by the mechanical or electronic linear scanning and the sector scanning can also be introduced.

FIG. 3 shows the time chart of FIG. 1 illustrating the principle of this invention. In FIG. 3, the transmitted wave and reflected waves corresponding to FIG. 1 are indicated on the time axis t.

Namely, the transducer 7 transmits the ultrasonic wave A1 having a frequency of 2 MHz as shown in FIG. 3(a), while the transducer 8 transmits the ultrasonic wave B1 having a frequency of 1 MHz as shown in FIG. 3(c). The reflected waves C11, C21, C31 can be obtained for the ultrasonic wave A1, while D11, D21, D31 for the ultrasonic wave B1. Thus, the received waves of the transducers 7, 8 are indicated as the combined reflected waves indicated in FIG. 3(a), (c). The received waves in frequencies corresponding to respective transmitted ultrasonic waves are separated and extracted from said combined ultrasonic wave signals by the transducers having the same frequency characteristics as the band-pass-filters of the frequencies (1 MHz and 2 MHz) which correspond to those of the transmitted ultrasonic waves.

Figure 4:
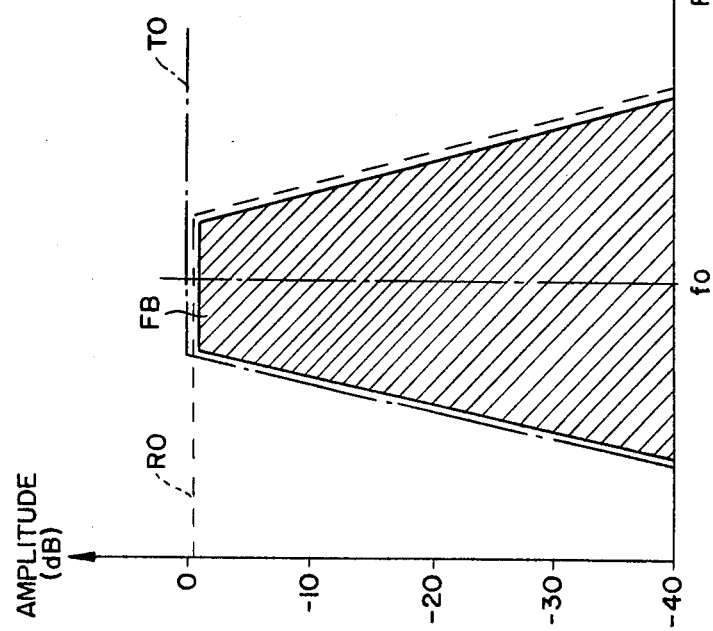
FIG. 4 graph of the frequency characteristic of the ultrasonic wave transducer used in the present invention.

FIG. 4 is a graph of the frequency characteristics (frequency vs. amplitude characteristics) of the ultrasonic wave transducers used in the present invention.

In the same figure, the horizontal axis f represents frequency, while the vertical axis represents amplitude level (dB). In principle, it is generally known that for the piezoelectric material used for the ultrasonic wave transducer, such as PZT, PVR etc., the transmission characteristic when converting an electrical signal to an ultrasonic wave signal at a frequency near the resonant frequency $f_0$ is indicated by the curve $T_0$, while the reception characteristic when converting an ultrasonic wave signal into an electrical signal is indicated by the curve $R_0$.

Therefore, when a piezoelectric element is used as the transducer of the ultrasonic imaging apparatus as explained above, for example, when transmission and reception of ultrasonic waves is carried out with only one transducer, such a transducer is equivalent to a filter having the band-pass FB. In addition, even when the transducer for transmission only and the transducer for reception only are individually provided, these transducers are equivalent to those having the signal pass-band FB because the transmission and reception characteristics of respective transducers are inherently combined.

Focusing on this point, the present invention operates to discriminate between different kinds of ultrasonic waves by using the transmission/reception characteristics of these transducers.

Figure 5:
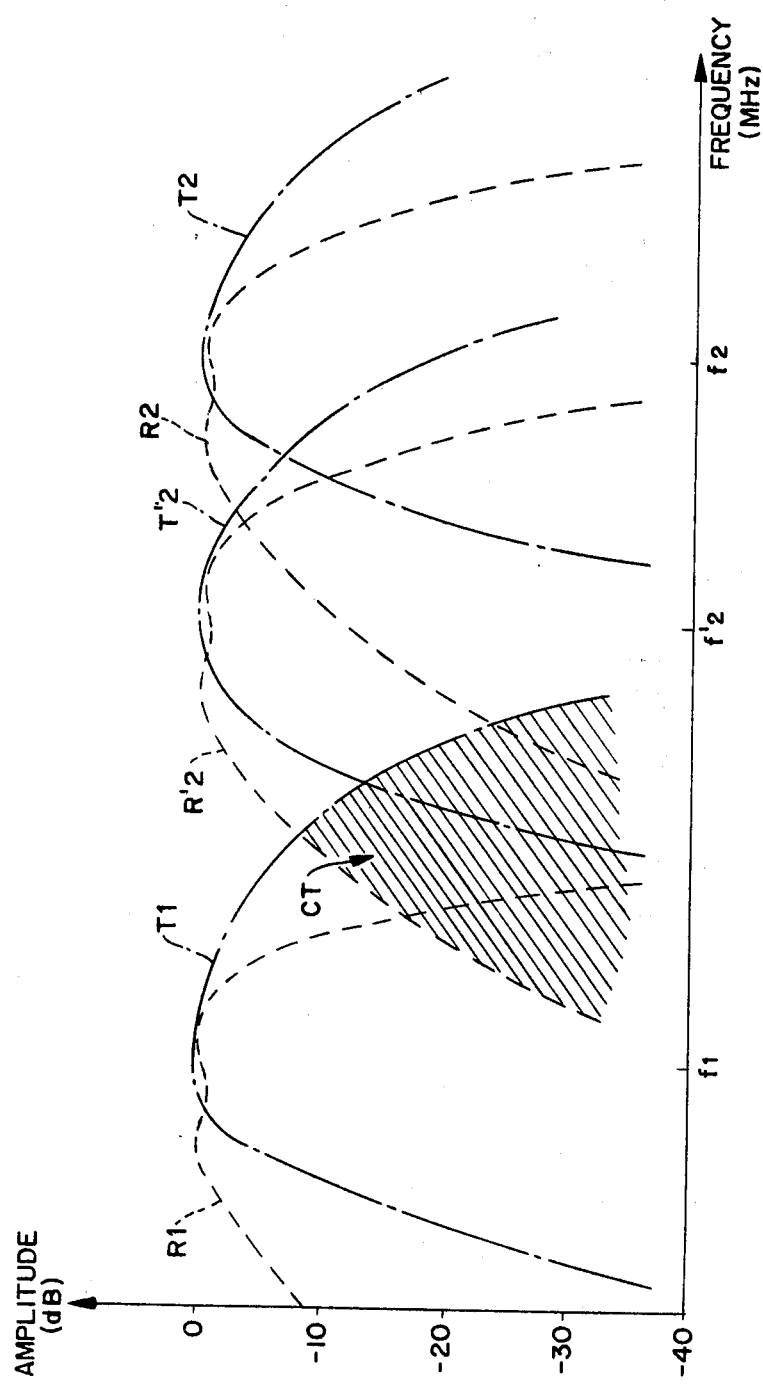
FIG. 5 is a graph of the frequency characteristics of two ultrasonic wave transducers used in the present invention.

FIG. 5 shows the frequency characteristics of the two transducers driven by the center frequencies $f_1$, $f_2$.

In the same figure, the curves R1, R2, R2' are reception characteristics, namely the electro-acoustic conversion frequency characteristics; the dash-dot-dash curves T1, T2, T2' are transmission characteristics, namely the electro-acoustic conversion frequency characteristics. Moreover, the curves R1, T1 are frequency characteristics of the 2nd transducer driven by the center frequency $f_1$, the curved R2, T2 are frequency characteristics of the 1st transducer driven by the center frequency $f_2$ and the curves R2', T2' are frequency characteristics of the 1st transducer driven by the center frequency $f_2'$.

In the same figure, the 2nd transducer (8 in FIG. 1, 10 in FIG. 2) which receives the ultrasonic wave signal with the center frequency $f_1$ does not receive the ultrasonic wave signal (T2) in frequency $f_2$ transmitted from the 1st transducer (7 in FIG. 1, 7' in FIG. 2) because of its reception characteristic (R1). Moreover, the 1st transducer (7 in FIG. 1, 9 in FIG. 2) which receives the ultrasonic wave signal with the center frequency $f_2$ does not receive the ultrasonic wave signal (T1) in the center frequency $f_1$ because of its reception characteristic (R2).

Therefore, in this case, a filter is no longer required in addition to the transducer and, moreover, the signals in respective bands can be distinguished between as the outputs.

On the other hand, when obtaining a tomographic image of the abdomen of a human body, it is undesirable to keep the frequency $f_1$ at a lower value in order to obtain a high time resolution and the frequency $f_2$ cannot be set too high because the attenuation coefficient is proportional to frequency. In such a case it is also undesirable to increase a difference between the frequencies $f_1$ and $f_2$. Therefore these frequencies are related as indicated by $f_1$, $f_2'$ shown in FIG. 5. Resultingly, the 1st reception element (7 in FIG. 1, 9 in FIG. 2) having the reception characteristic R2' generates crosstalk wherein the signal containing the signal component CT transmitted from the 2nd transmission element (8 in FIG. 1, 8' in FIG. 2) is output as an electrical signal. In order to suppress the crosstalk (CT), an electrical filter is provided to any one (or both) of the transmission means connected to the transmission element and the reception means connected to the reception element.

FIG. 6 is a graph of the frequency characteristic where an electric filter is connected to the one reception element used in the present invention.

An electric filter is connected to the 1st reception element and the characteristic indicated by the line LF of the electric filter is added to the reception characteristic R2' of the 1st reception element. As another example, a filter having the characteristic of reducing the signal component received by the reception characteristic R2' for the transmission characteristic T1 may be added in the transmission means side of the 2nd transmission element.

The preferred embodiment of the present invention will be explained below.

In the following explanation of the embodiment, the reflected wave is considered as the received wave, but it is also possible to use transmitted waves or diffracted waves as the received wave.

FIG. 11 shows the block diagram of an embodiment of the present invention. In the same figure, 1 is the transmission unit; 2 is the reception gate unit; 3 is the reception processing unit; 4 is the display control unit; 5 is the display unit; 6 is the control unit; 7 is the 1st transducer unit; and 8 is the 2nd transducer unit.

The 1st transducer unit 7 is composed of five transducers 7a, 7b, 7c, 7d, 7e while the 2nd transducer unit 8 is also composed of five transducers 8a, 8b, 8c, 8d, 8e. These units are well known array type electro-acoustic conversion elements.

This array type electro-acoustic conversion element is configured with piezoelectric elements which transmit the ultrasonic waves according to the given transmitting frequency signals and which also generate electrical signals according to the reflected waves received from the specimen X. The transducers 7a to 7e have the transmission and reception frequency characteristics T2', R2' shown in FIG. 5, while the transducers 8a to 8e have the transmission and reception frequency characteristics T1, R1 shown in FIG. 5.

The transmission unit 1 includes 1st and 2nd transmission selectors 11 and 12, and the 1st transmission selector 11 corresponds to the 1st transducer unit 7, while the 2nd transmission selector 12 corresponds to the 2nd transducer unit 8.

Each of the transmission selectors 11 and 12 has one input terminal and five output terminals, and the five output terminals of the 1st transmission selector 11 are respectively connected to each of the transducers 7a to 7e of the 1st transducer unit 7. Each of five output terminals of the 2nd transmission selector 12 is connected to each of the transducers 8a to 8b of the 2nd transducer unit 8. The input terminals of the transmission selectors 11 and 12 are respectively connected to 1st and 2nd signal generator circuits (transmission circuit) 13 and 14. The input terminal and output terminal of each transmission selector 11 and 12 are connected by means a the rotary arm, which sequentially and selectively connects the input and output terminals in accordance with the instruction sent from a selection circuit 15.

The transmission selectors 11 and 12 are explained using the rotary arm and contact for easy understanding, but it is desirable to use a well known selector circuit having a gate circuit structure.

The selection circuit 15 changes the connections of the transmission selectors 11 and 12 according to an instruction given from a control unit 6, and the 1st and 2nd signal generator circuits 13 and 14 output the signals for generating the ultrasonic waves A and B by receiving instructions given from the control unit 6.

Therefore, in transmission unit 1, the 1st signal generator circuit 13 outputs a signal for transmitting the ultrasonic wave A of frequency $f_2'$, while the 2nd signal generator circuit 14 outputs a signal for transmitting the ultrasonic wave B of frequency $f_1$; both operations are initiated by receiving an instructions from the control unit 6. These signals are sent to the specific predetermined transducers 7a to 7e, 8a to 8e being connected to the selection output terminals of the transmission selectors 11 and 12 in accordance with an instruction sent from the selection circuit 15.

Figure 7:
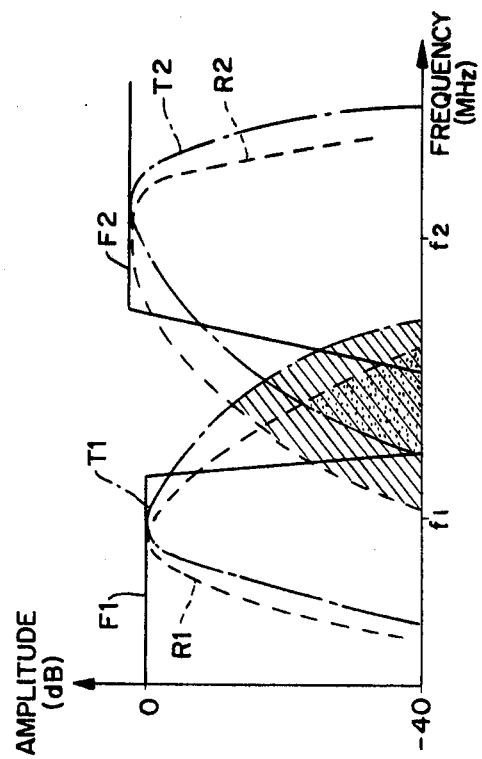

In FIG. 7, the transducers 7a and 8a are selected and the ultrasonic wave A is transmitted from the transducer 7a, while the ultrasonic wave B is transmitted from the transducer 8a, simultaneously.

According to instruction sent from the selection circuit 15, the transmission selectors 11 and 12 select the 2nd output terminals and therefore the 1st and 2nd signal generator circuits 13, 14 are respectively connected to the transducers 7b, 8b. Then, when an instruction is received from the control unit 6, the output signals corresponding to the ultrasonic waves A, B are generated from the 1st, 2nd signal generator circuits 13, 14 and thereby the ultrasonic waves A, B are transmitted from the transducers 7b, 8b.

In the above-desired embodiment, so-called electronic linear scanning is performed simultaneously by two transducers.

The transmission time chart of the transducers 7, 8 at their respective frequencies is shown in FIG. 3.

The transmission period from the transducer 7a to 7b is the same as that of existing methods.

For the 1st and 2nd signal circuits 13, 14, the impulse drive is carried out. These are not explained in detail because well known circuit structures are employed.

The reflected waves of the ultrasonic waves which are thus transmitted by the transmission unit 1 are processed by the reception gate unit 2 and reception processing units.

The 1st reception circuit is composed of the 1st reception selector 21, 1st gain compensating circuit 23, extraction filter 31 and 1st shift register 32. The 2nd reception circuit is composed of the 2nd reception selector 22, 2nd gain compensating circuit 24 and 2nd shift register 33.

The reception gate unit 2 includes the 1st and 2nd reception selectors 21 and 22, and the 1st reception selector 21 corresponds to the 1st transducer unit 7, while the 2nd reception selector 22 corresponds to the 2nd transducer 8.

The reception selectors 21 and 22, respectively, have one output terminal and five input terminals. Each of five input terminals of the 1st reception selector 21 is connected to one transducer 7a to 7e of the 1st transducer unit 7. Each of five input terminals of the 2nd reception selector 22 is connected to one transducer 8a to 8e of the 2nd transducer unit 8. The output terminals of the reception selectors 21, 22 are respectively connected to the 1st and 2nd gain compensating circuits 23 and 24.

These circuits are connected to the input terminals of the reception selectors 21, 22 by means of rotary arms, which sequentially and selectively connect the input and output terminals according to an instruction given from a selection circuit 25. The reception selectors 21 and 22 are explained using the rotary arm and contact for easy understanding. But, it is desirable to use a well known select circuit having a gate circuit structure. The selection circuit 25 changes the connections of the reception selectors 21 and 22 according to an instruction sent from the control unit 6. The gain compensating circuits 23, 24 compensate for attenuation by changing the gain on a time basis because the reflected wave returning from the further areas in the specimen show a larger attenuation. The gain compensating circuits 23 and 24 change the gain on a time basis in dependence upon an instruction generated by the control unit 6 after it has generated an instruction for outputting the ultrasonic waves.

Therefore, the reception gate unit 2 connects gain compensation circuits 23, 24 to the selective input terminals of the reception selectors 21 and 22 according to an instruction sent from the selection circuit 25. The electrical signals obtained from the reflected waves sent from the transducers 7a to 7e, 8a to 8e are respectively input to the gain compensating circuits 23, 24.

In FIG. 11, the transducers 7a, 8a are selected and an electrical signal corresponding to the reflected wave received from the transducer 7a is input to the gain compensating circuit 23, while an electrical signal corresponding to the reflected wave received from the transducer 8a is input to the gain compensating circuit 24.

The reception selectors 21 and 22 sequentially select, like the transmission selectors 11 and 12, the transducers 7b and 8b, 7c and 8c, 7d and 8d, 7e and 8e, for the electronic scanning in synchronization with the selecting operation of the transmission selectors.

C11 to C31, D11 to D31 in FIG. 3 respectively show the received ultrasonic waves of the transducers 7a to 8a. The outputs of the gain compensating circuit 23 and 24 are input to the reception processing unit 3.

The reception processing unit 3 comprises the extraction filter 31 having the characteristics shown as LF in FIG. 6 and the 1st and 2nd shift registers 32, 33. The extraction filter 31 extracts only the reflected wave corresponding to the transmitted ultrasonic wave, namely the ultrasonic wave with the center frequency $f_2'$ shown in FIG. 6 and then sends it to the shift register 32 after the analog-to-digital conversion. On the other hand, as illustrated in FIG. 5, the output signal from transducer 8 contains only the reflected waves corresponding to the ultrasonic wave B namely the ultrasonic wave with the center frequency $f_1$ sent to the shift register 33 after the analog-to-digital conversion.

Therefore, only those waves corresponding to its own transmitting frequencies among the reflected waves received by the transducer unit 7 are perfectly extracted by the filter function having the reception characteristics $R_2'$ (FIG. 6) of the transducers 7a to 7e and the extraction filter 31 having the filter characteristic LF (FIG. 6). On the other hand, those waves corresponding to the transmitting frequency of the transducer unit 8 among the reflected waves received by the transducer unit 8 are extracted by the filter having the reception characteristic R1 (FIG. 5) of the transducers 8a to 8e.

The data thus stored in the shift registers 32, 33 are digital values of the time series reflected waves for the transmitted ultrasonic waves. At this time, the time series digital values are input to the display control unit 4 for display on the display unit 5.

The display control unit 4 is composed of a screen memory 41 a write circuit 40 and a display control circuit 42. The write circuit 40 writes the output signals of the two shift registers 32 and 33 in the corresponding location of the screen memory 41 according to the location of the transducers 7a to 7e, 8a to 8e.

The display control circuit 42 transmits the stored information of the screen memory 41 according to the scanning timing of the display unit 5, causing it to display a tomographic image using the time series reflected waves.

The ultrasonic waves A, B are transmitted, the reflected waves of them are received and a tomographic image is displayed on the display unit through separation and extraction.

In the above embodiment, the high-pass filtering function is provided for one received signal on the reception side, but other methods may be employed.

FIGS. 12(a), (b) is a graph of the frequency characteristics of an other embodiment of the present invention. In these figures, the same portions as those in FIG. 5 are given the same symbols. Namely, in the case of FIG. 12(a), a filter having the filtering characteristic LF' is inserted between the 2nd signal circuit 14 and the transducer unit 8 of the transmission unit 1. In this embodiment, the filter 31 can be removed but when it is used, the crosstalk can be eliminated perfectly as shown in FIG. 7.

In this case, the transmission spectrum SA1 exists at least in the band which is not extracted by the reception characteristic R2 of the transducer 7.

FIG. 12(b) shows the frequency characteristics when three transducer units are used. The bands of two transmitting signals are defined by the hatched areas SA1 and SA2 by means of the filter characteristics LF1, LF2, and these signals are received discriminatingly by limiting one signal to the band SA3 determined by the characteristics of the transducer.

Therefore, even when the filters are used in the transmission or reception circuit, the number of filters can be reduced as long as the filtering characteristic of the transducer are utilized for the discrimination of signals.

FIG. 7 is a graph of the characteristic of an example where the electrical filter is connected to both the 1st, 2nd reception element in the present invention.

In the examples of FIG. 6 and FIG. 11, the electrical filter is provided in the reception element of the 1st reception element in order to cut the signal having the frequency $f_1$ in the 1st reception element. When the bandwidth of a transducer becomes narrow, as shown in FIG. 7, the characteristic T2 of the 1st transmission element and the characteristic R1 of the 2nd reception element overlap, thus causing the crosstalk.

Therefore, such crosstalk is prevented by also providing the electrical filter having the characteristic indicated by F1 in FIG. 7 in the reception circuit of the 2nd reception element.

It is also possible to provide the electrical filter having the characteristic indicated by F2 in FIG. 7 to the transmission element.

Moreover, it is more desirable, in some cases, to replace the electrical filter with a band pass filter.

Figure 8:
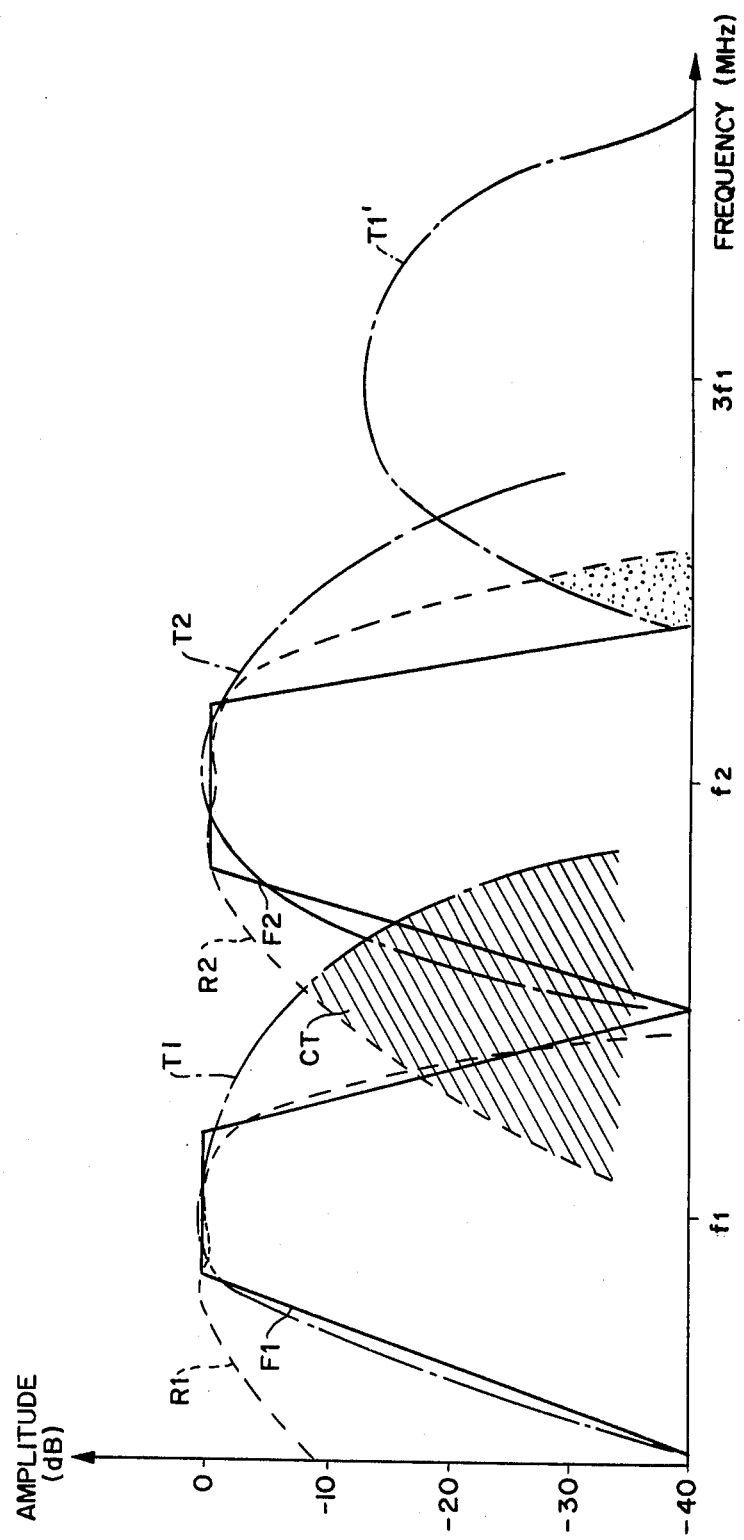
FIG. 8 is a graph of the frequency characteristics when a band-pass-filter is connected according to the present invention.

FIG. 8 shows the characteristic when a band pass filter is used in the present invention.

Namely, the 2nd electrical filter having the characteristic F1 is connected to the 2nd reception element, while the 1st filter having the characteristic F2 is connected to the 1st reception element, thereby improving the efficiency of crosstalk elimination. For example, the center frequency of a transducer can be determined depending on the thickness of piezoelectric material. Therefore, as shown in FIG. 8 for example, the transmission spectrum of the 2nd transmission element is accompanied by harmonics $T_1'$ ($3f_1$) in addition to $T_1$. The component $T_1$ enters the reception signal of the 1st reception element. Such a component can be eliminated by desirably using the band pass filter in place of the 1st electrical filter. It is also recommended that a band pass filter be employed in place of the 2nd electrical filter in order to efficiently eliminate unwanted noise.

The crosstalk elimination effect becomes perfect when an electrical filter is connected to each of the 1st, 2nd transmission elements and the 1st, 2nd reception elements.

Attenuation is more pronounced on the higher frequency side than the lower frequency side. The method of compensating such attenuation will be explained below.

Figure 9:
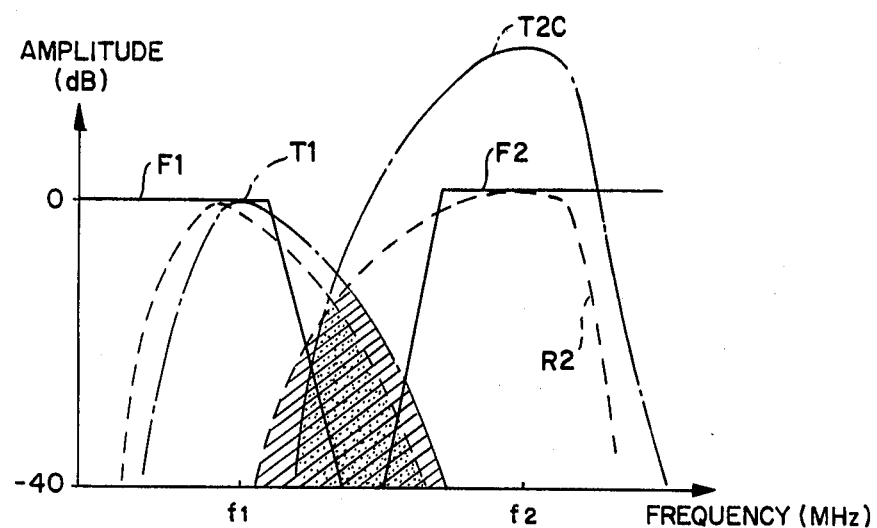
FIG. 9 is a graph of the frequency characteristics when the high frequency component is compensated according to the present invention.

FIG. 9 is a graph of the frequency characteristic when measures for reducing attenuation are introduced by the present invention.

The transmission level of the 1st transmission element is raised as shown in $T_2C$, higher than that in FIG. 7. This is done by raising the transmission level of the signal generator circuit 13 shown in FIG. 11. Thus, the high frequency side $f_1$ is higher in level than the low frequency side $f_2$, thereby compensating for attenuation of the high frequency component.

Figure 10A:
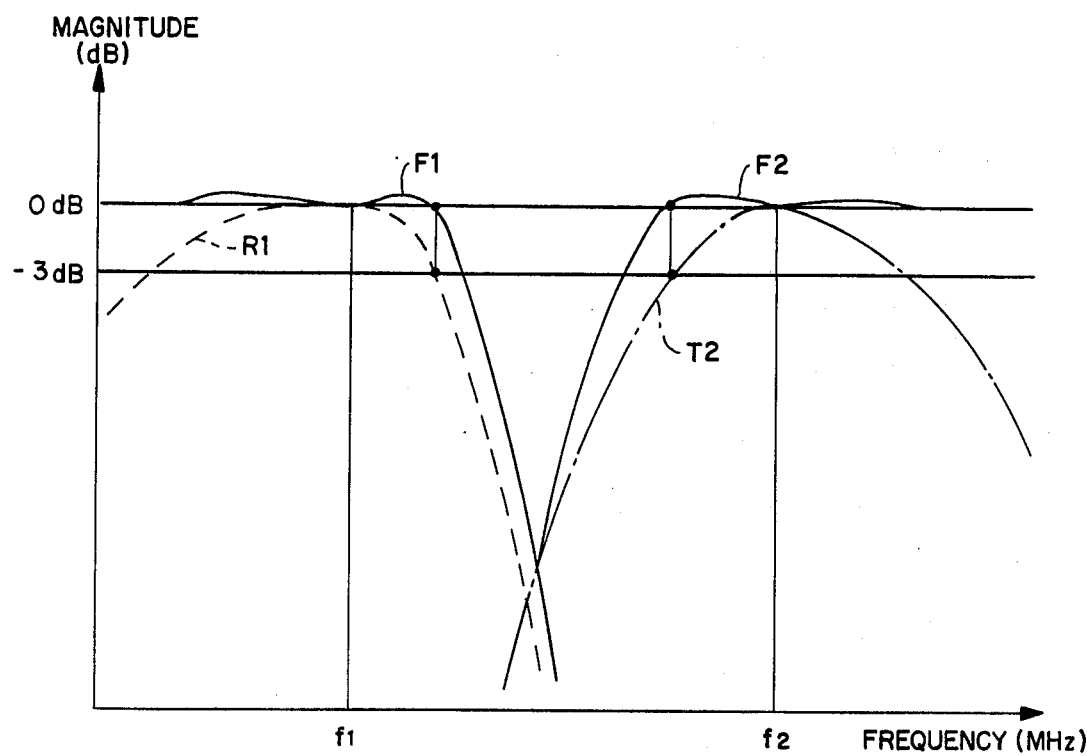

FIGS. 10A and 10B are graphs of the characteristics of electrical filters used in the present invention. In FIG. 10A, an electrical filter having the characteristic $F_2$ is connected to the 1st transmission element, while an electrical filter having the characteristic $F_1$ is connected to the 2nd reception element. An electrical filter is so designed that the characteristic is substantially flat up to the frequency corresponding to $-3$ dB of the transmission, reception characteristics T2, R1 but shows predetermined slope at the frequency corresponding to the lower level than −3 dB.

This characteristic assures a wide band and sufficient cut-off capability of the filter.

FIG. 10B shows the characteristic obtained by connecting an electrical filter having the characteristic $F_2'$ to the 1st reception element and an electrical filter having the characteristic $F_1'$ to the 2nd transmission element.

In this case, an electrical field is designed so that the characteristic is flat up to the frequency corresponding to −3 dB of the reception, transmission characterisic R2, T1, but shows predetermined slope as in the case of FIG. 10A, at the frequency corresponding to the level lower than −3 dB.

On the other hand, the filtering effect as a system is determined by multiplication of the characteristics. Therefore, the transmission characteristic becomes $F_1' \times T_1$, while the reception characteristic becomes $F_2' \times R_2$. When the filters provided as shown in FIG. 10A, 10B are adopted, a characteristic assuring having a wide frequency band and little crosstalk can be obtained.

In the above embodiment, an impulse signal is used as the transmitted ultrasonic waves, but other various kinds of signals such as burst wave signal, sharp modulated wave signal, etc., can also be used.

As explained previously, the signal components in the different frequency bands of the ultrasonic wave band can be separated and output according to the present invention. Therefore, a plurality of specimen data can be obtained simultaneously. This is very effective for diagnostic operation from medicine or in the industrial viewpoint.

We claim:

1. An ultrasonic imaging apparatus for imaging the internal structure of an object by transmitting ultrasonic waves to said object and receiving acoustic waves from said object, comprising:
   at least two transducers for transmitting ultrasonic waves and receiving acoustic waves, said at least two transducers having different frequency characteristics and functioning as frequency filters on the basis of their respective frequency characteristics;
   a first transmission circuit, connected to a first of said at least two transducers, for causing said first transducer to transmit ultrasonic waves at a first frequency;
   a first reception circuit connected to said first transducer;
   a second transmission circuit connected to a second of said at least two transduces, for causing said second transducer to transmit ultrasonic waves at a second frequency different from said first frequency;
   a second reception circuit connected to said second transducer; and
   an electric filter provided in at least one of said first transmission circuit and said second reception circuit.

2. An ultrasonic imaging apparatus according to claim 1, wherein said first frequency is higher than said second frequency, wherein said first transducer has a first reception frequency characteristic, wherein said second transducer has a second reception frequency characteristic partly overlapping said first reception frequency characteristic, and wherein said electric filter has a characteristic which functions to eliminate such overlap.

3. An ultrasonic imaging apparatus according to claim 2, wherein said electric filter is provided in both said 1st transmission circuit and said second reception circuit.

4. An ultrasonic imaging apparatus according to claim 2, wherein said electric filter is provided in both said second reception circuit and said first reception circuit.

5. An ultrasonic imaging apparatus according to claim 2 wherein said electric filter is provided in both said first transmission circuit and said second transmission circuit.

6. An ultrasonic imaging apparatus according to claim 3 wherein said electric filter is further provided in both said second transmission circuit and said 1st reception circuit.

7. An ultrasonic imaging apparatus as claimed in claim 2, 3, 4, 5, or 6, wherein said first transducer comprises at least one emitting transducer and at least one receiving transducer positioned so that the ultrasonic waves emitted by said emitting transducer are detected by said receiving transducer wherein the detected ultrasonic waves are diffracted ultrasonic waves and directly transmitted ultrasonic waves.

8. An ultrasonic imaging apparatus as claimed in claim 7, wherein said emitting transducer and said receiving transducer are positioned adjacent to each other.

9. An ultrasonic imaging apparatus as claimed in claim 7, comprising a plurality of said emitting transducers for transmitting ultrasonic waves simultaneously.

10. An ultrasonic imaging apparatus as claimed in claim 1, 2, 3, 4, 5 or 6, wherein said electric filter is a band-pass filter.

11. An ultrasonic imaging apparatus as claimed in claim 1, 2, 3, 4, 5 or 6, wherein said first frequency is higher than said second frequency, and wherein the magnitude of said first frequency ultrasonic waves is increased so as to compensate for attenuation characteristics of said first frequency waves.

12. An ultrasonic imaging apparatus as claimed in claim 1, 2, 3, 4, 5 or 6, wherein said at least two transducers are piezoelectric devices.

13. An ultrasonic imaging apparatus for imaging the internal structure of an object by transmitting ultrasonic waves to the object and receiving acoustic waves from the object, comprising:
   first means for generating first and second transducer control signals;
   a first transducer unit, operatively connected to said first means, for transmitting ultrasonic waves at a first frequency in dependence upon said first transducer control signal and for receiving acoustic waves, said first transducer unit having a first frequency characteristic and functioning as a frequency filter on the basis of the first frequency characteristic;
   a second transducer unit, operatively connected to said first means, for transmitting ultrasonic waves at a second frequency in dependence upon said second transducer control signal and for receiving acoustic waves, said second transducer unit having a second frequency characteristic different from the first frequency characteristic, said second transducer unit functioning as a frequency filter on the basis of the second frequency characteristic;

second means, operatively connected to said first and second transducer units, for receiving the acoustic waves received by said first and second transducer units and for generating first and second detection signals, respectively;

an electric filter, connected to said second means, for receiving and filtering at least one of said first and second detection signals; and third means, operatively connected to said second means and said electric filter, for displaying the internal structure of the object.

* * * * *

UNITED STATES PATENT AND TRADEMARK OFFICE
CERTIFICATE OF CORRECTION

PATENT NO. : 4,413,520       Page 1 of 4

DATED : NOVEMBER 8, 1983

INVENTOR(S) : KEIICHI MURAKAMI ET AL.

It is certified that error appears in the above-identified patent and that said Letters Patent is hereby corrected as shown below:

```
FRONT PAGE [30] FOREIGN APPLICATION PRIORITY DATA
                "56-21655" should be --55-81799--.

[57] ABSTRACT
                line 3, after "acoustic" insert --waves--;
                line 5, after ".", continue with line 6.

Col. 1, line 7, delete "developing"; and
                   "imaging" should be --developing--;
           line 64, after "number" insert --of--.

Col. 3, line 17, delete "shows";
           line 18, after "of" insert --a--;
           line 47, after "4" insert --is a--;
           line 66, after ";" insert --and--.

Col. 4, line 19, "electical" should be --electrical--;
           line 28, delete "those";
           line 34, after "instead" insert --of--.
```

UNITED STATES PATENT AND TRADEMARK OFFICE
CERTIFICATE OF CORRECTION

PATENT NO. : 4,413,520

DATED : NOVEMBER 8, 1983

INVENTOR(S) : KEIICHI MURAKAMI ET AL.

It is certified that error appears in the above-identified patent and that said Letters Patent is hereby corrected as shown below:

```
Col. 5, line 64, "curved" should be --curves--.

Col. 7, line 21, before "a" insert --of--;
        line 23, "the" should be --an--;
        line 36, "f2'" should be --f'2--;
        line 39, delete "an";
        line 61, after ".", continue with line 62;
        line 63, after ".", continue with line 64.

Col. 8, line 4, "units" should be --unit 3--; and
                after ".", continue with line 5;
        line 25, after ".", continue with line 26;
        line 45, after ".", continue with line 46;
        line 46, after "connects" insert --the--.

Col. 9, line 32, "41" should be --41,--;
        line 36, after ".", continue with line 37;
        line 50, "an other" should be --another--;
        line 58, after ".", continue with line 59;
        line 68, after ".", continue with Col. 10, line 1.
```

UNITED STATES PATENT AND TRADEMARK OFFICE
CERTIFICATE OF CORRECTION

PATENT NO. : 4,413,520   Page 3 of 4
DATED : NOVEMBER 8, 1983
INVENTOR(S) : KEIICHI MURAKAMI ET AL.

It is certified that error appears in the above-identified patent and that said Letters Patent is hereby corrected as shown below:

Col. 10, line 1, delete indentation;
line 3, "characteristic" should be --characteristics--;
line 4, "transducer" should be --transducers--;
line 9, "element" should be --circuit--;
line 15, after ".", continue with line 16;
line 19, after ".", continue with line 20;
line 22, after ".", continue with line 23;
line 25, "characteristic" should be --characteristics--;
line 26, after ".", continue with line 27;
line 46, after ".", continue with line 47.

Col. 11, line 3, after ".", continue with line 4;
line 10, after ".", continue with line 11;
line 11, "field" should be --filter--;
line 34, "from" should be --in--; and "in" should be --from--.

UNITED STATES PATENT AND TRADEMARK OFFICE
CERTIFICATE OF CORRECTION

PATENT NO. : 4,413,520         Page 4 of 4
DATED     : NOVEMBER 8, 1983
INVENTOR(S) : KEIICHI MURAKAMI ET AL.

It is certified that error appears in the above-identified patent and that said Letters Patent is hereby corrected as shown below:

Col. 12, line 5, "1st" should be --first--;
         line 17, "1st" should be --first--;
         line 25, "transducer" should be --transducer,--.

Signed and Sealed this

Twenty-ninth Day of May 1984

[SEAL]

Attest:

GERALD J. MOSSINGHOFF

*Attesting Officer*         *Commissioner of Patents and Trademarks*